United States Patent
Umetsu et al.

(10) Patent No.: US 7,307,444 B2
(45) Date of Patent: Dec. 11, 2007

(54) TESTING METHOD AND TESTING APPARATUS FOR LIQUID CRYSTAL PANEL

(75) Inventors: Kazushige Umetsu, Nagano (JP); Shuhei Yamada, Nagano (JP)

(73) Assignee: Seiko Epson Corporation (JP)

( * ) Notice: Subject to any disclaimer, the term of this patent is extended or adjusted under 35 U.S.C. 154(b) by 62 days.

(21) Appl. No.: 11/190,029

(22) Filed: Jul. 26, 2005

(65) Prior Publication Data
US 2006/0055931 A1    Mar. 16, 2006

(30) Foreign Application Priority Data
Sep. 13, 2004    (JP) .................. 2004-265096

(51) Int. Cl.
*G01R 31/00*    (2006.01)
(52) U.S. Cl. .................. 324/770; 356/432
(58) Field of Classification Search ............. 324/750, 324/752, 770; 356/432; 349/187, 192
See application file for complete search history.

(56) References Cited

U.S. PATENT DOCUMENTS

| | | | | |
|---|---|---|---|---|
| 4,189,641 | A * | 2/1980 | Katagiri et al. | 250/311 |
| 5,621,334 | A * | 4/1997 | Urano et al. | 324/770 |
| 6,097,462 | A * | 8/2000 | Koe | 349/123 |
| 6,700,679 | B1 * | 3/2004 | Fujita et al. | 358/1.9 |
| 6,724,215 | B2 * | 4/2004 | Kuroiwa | 324/770 |
| 7,157,921 | B2 * | 1/2007 | Shonohara | 324/751 |

FOREIGN PATENT DOCUMENTS

| | | |
|---|---|---|
| JP | H07-060471 | 3/1995 |
| JP | 2001-004526 | 1/2001 |
| JP | 2001-110861 | 4/2001 |
| JP | 2001-215108 | 8/2001 |
| JP | 2002-196344 | 7/2002 |
| JP | 2003-043504 | 2/2003 |
| JP | 2004-258613 | 9/2004 |
| WO | 02/057839 | 7/2002 |

OTHER PUBLICATIONS

Communication from Japanese Patent Office regarding corresponding application, 2006.

* cited by examiner

*Primary Examiner*—Ha Tran Nguyen
*Assistant Examiner*—Arleen M. Vazquez
(74) *Attorney, Agent, or Firm*—Harness, Dickey & Pierce, P.L.C.

(57) ABSTRACT

The present invention provides a technique enabling the amount of time required to evaluate the light fastness of a liquid crystal panel to be shortened. A method of testing the light fastness of a liquid crystal panel comprising a pair of substrates and a liquid crystal layer interposed between the substrates comprises the steps of: irradiating a test subject area of the liquid crystal panel with a laser beam, with at least one of the wavelength, the irradiation energy, and the irradiation duration of the laser beam set as a variable parameter; irradiating the liquid crystal panel with an observation beam and detecting the condition of the observation beam after passing through the liquid crystal panel; and evaluating the light fastness of the liquid crystal panel on the basis of a difference in the condition of the observation beam corresponding to the setting of the variable parameter of the laser beam.

6 Claims, 7 Drawing Sheets

TESTING METHOD AND TESTING APPARATUS FOR LIQUID CRYSTAL PANEL

RELATED APPLICATIONS

This application claims priority to Japanese Patent Application No. 2004-265096 filed Sep. 13, 2004 which is hereby expressly incorporated by reference herein in its entirety.

BACKGROUND OF THE INVENTION

1. Field of the Invention

The present invention relates to a testing method and testing apparatus for evaluating the light fastness of a liquid crystal panel.

2. Description of the Related Art

Conventionally, a light fastness test is performed on a liquid crystal panel as a way of evaluating the reliability of the liquid crystal panel. For example, when a liquid crystal panel used as a light bulb in a liquid crystal projector is irradiated with intense light over a long time period, the various constitutional elements (components, members) thereof are likely to deteriorate, and it is therefore important to perform a light fastness test to ensure the required quality of these elements.

To test the light fastness of such a liquid crystal panel, a test period of up to several months may be required after the order is made. However, with demands being made for ever shorter product development periods, such a long test period is unacceptable. In response, a so-called acceleration test, in which a test is performed under more severe conditions than an actual usage situation and deterioration over long-term usage is predicted on the basis of the test results, is known as a method of shortening the evaluation period. The prior art relating to this type of light fastness evaluation of a liquid crystal panel is disclosed in Japanese Unexamined Patent Application Publication 2001-4526, for example.

In a conventional light fastness evaluation method such as that described above, a liquid crystal panel is irradiated with light using a light source such as a metal hydride lamp, UHP lamp, or halogen lamp. However, the light obtained from these light sources is poorly condensed, and hence a high energy density cannot be obtained. As a result, it is difficult to elicit a deterioration phenomenon in a short amount of time. Thus a problem arises in that a long time period is required to evaluate the light fastness of the liquid crystal panel. This long evaluation period makes it difficult to reduce the product development period, which is undesirable.

SUMMARY OF THE INVENTION

It is therefore an object of the present invention to provide a technique enabling the amount of time required to evaluate the light fastness of a liquid crystal panel to be shortened.

A first aspect of the present invention is a method for testing the light fastness of a liquid crystal panel comprising a pair of substrates and a liquid crystal layer interposed between the substrates, comprising the steps of: irradiating a test subject area of the liquid crystal panel with a laser beam, with at least one of the wavelength, the irradiation energy, and the irradiation duration of the laser beam set as a variable parameter; irradiating the liquid crystal panel with an observation beam and detecting the condition of the observation beam after passing through the liquid crystal panel; and evaluating the light fastness of the liquid crystal panel on the basis of a difference in the condition (the optical intensity, polarization state, and so on) of the observation beam corresponding to the setting of the variable parameter of the laser beam.

With this method, a laser beam is used as the light for checking the light fastness of the liquid crystal panel, and therefore light irradiation can be performed with a higher localized energy density than a case where a halogen lamp or the like is used as a light source. As a result, a deterioration phenomenon can be elicited in an extremely short time (between several minutes and several tens of minutes, for example), and the light fastness of the liquid crystal panel can be evaluated by investigating the correlation between the irradiation conditions of the laser light during the irradiation and the degree of deterioration produced by the irradiation. Hence, the amount of time required to evaluate the light fastness of the liquid crystal panel can be reduced greatly.

In the first step of those described above, the alignment of the liquid crystal layer in the test subject area is preferably caused to deteriorate locally upon irradiation with the laser beam. In particular, it is preferable that an alignment layer within the test subject area be altered such that the alignment regulating force of the alignment layer is decreased or eliminated.

In so doing, it is possible to evaluate the deterioration of the liquid crystal panel caused by the decrease in alignment produced by light irradiation.

In the second step of those described above, a polarization element is preferably disposed on at least a light exit side of the liquid crystal panel, and the optical intensity of the observation beam after passing through the polarization element is preferably detected as the condition of the observation beam.

When a polarization element is used, variation in the alignment state of the liquid crystal layer produced by deterioration of the liquid crystal panel can be detected easily as variation in the optical intensity of the transmitted light.

Further, it is preferable that the laser beam double as the observation beam, and the first step and second step be performed in parallel.

In so doing, the evaluation period can be shortened even further. Moreover, the apparatuses, instruments, and so on used to implement the testing method can be simplified.

Further, a continuous wave is preferably used as the laser beam.

In so doing, energy can be applied to the test subject area efficiently, and hence the test subject area can be caused to deteriorate efficiently. As a result, a further reduction in the test duration can be achieved.

In the first step of those described above, the test subject area is preferably irradiated with the laser beam via an image-forming optical system.

In so doing, energy can be applied uniformly over the entire test subject area, enabling an improvement in the reliability of the evaluation result.

Also in the first step of those described above, the test subject area is preferably irradiated with the laser beam via a condensing optical system.

In this case, the evaluation can be performed in a much smaller test subject area. This is effective when an evaluation is to be performed selectively on a specific constitutional element of the liquid crystal panel, for example (when an evaluation is to be performed only within the pixel electrode, for example).

A second aspect of the present invention relates to a preferred testing apparatus used to implement the testing method according to the first aspect described above. More specifically, a liquid crystal panel testing apparatus according to the present invention is used for testing the light fastness of a liquid crystal panel comprising a pair of substrates and a liquid crystal layer interposed between the substrates, and comprises: a laser oscillator capable of outputting a laser beam with at least one of the wavelength, the irradiation energy, and the irradiation duration of the laser beam set as a variable parameter; position setting means for performing relative position setting between the laser beam and the liquid crystal panel such that a test subject area of the liquid crystal panel is irradiated with the laser beam output from the laser oscillator; observation beam output means for irradiating the liquid crystal panel with an observation beam used to measure the light transmission condition of the liquid crystal panel; and detection means for detecting the condition of the observation beam after passing through the liquid crystal panel.

By using the testing apparatus constituted as described above, the time required to evaluate the light fastness of the liquid crystal panel can be reduced greatly.

The testing apparatus preferably further comprises a polarization element disposed on at least a light exit side of the liquid crystal panel such that the detection means detect the optical intensity of the observation beam after passing through the polarization element as the condition of the observation beam.

Thus the condition of the observation beam can be detected easily.

Further, the laser beam preferably doubles as the observation beam.

Thus the constitution of the apparatus can be simplified.

Further, the laser beam is preferably set as a continuous wave.

In so doing, energy can be applied to the test subject area efficiently, and hence the test subject area can be caused to deteriorate efficiently. As a result, a further reduction in the test duration can be achieved.

The testing apparatus preferably further comprises an image-forming optical system for forming an image of the laser beam on the test subject area.

Thus, energy can be applied uniformly over the entire test subject area, enabling an improvement in the reliability of the evaluation result.

Also, the testing apparatus preferably further comprises a condensing optical system for condensing the laser beam on the test subject area.

In this case, the evaluation can be performed in a much smaller test subject area. This is effective when an evaluation is to be performed selectively on a specific constitutional element of the liquid crystal panel, for example.

DESCRIPTION OF THE DRAWINGS

In order that the invention may be readily carried into effect, it will now be described with reference to the accompanying drawings, wherein.

DETAILED DESCRIPTION

Embodiments of the present invention will be described below with reference to the drawings.

FIG. 1 is a schematic view illustrating a liquid crystal panel testing method. The testing method of this embodiment is applied to test the light fastness of a liquid crystal panel comprising a pair of substrates and a liquid crystal layer interposed between the substrates. In this testing method, the liquid crystal panel is caused to deteriorate by irradiating the liquid crystal panel with a laser beam, whereupon the liquid crystal panel is irradiated with an observation beam and observed optically to evaluate the degree of deterioration in the liquid crystal panel.

Figure 1A:
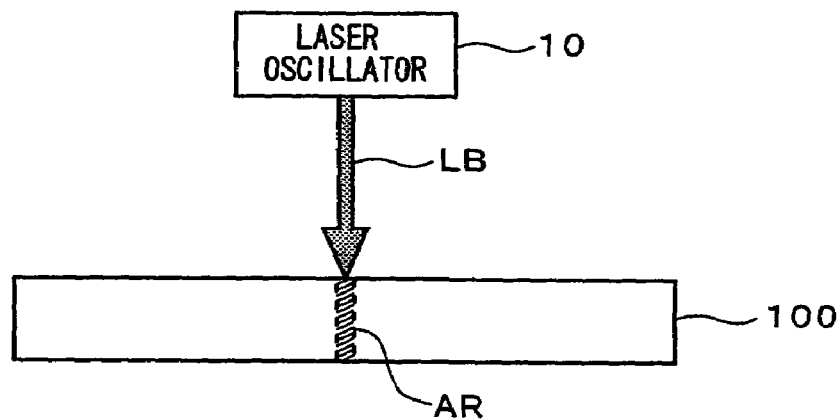
FIG. 1 is a schematic view illustrating a liquid crystal panel testing method.

More specifically, first, as shown in FIG. 1A, a test subject area AR of a liquid crystal panel 100 is irradiated with a laser beam LB, with at least one of the wavelength, irradiation energy, and irradiation duration of the laser beam LB set as a variable parameter (first step). A laser oscillator 10 is used to generate the laser beam LB. The test subject area AR may be set arbitrarily, for example as an area corresponding to a single pixel of the liquid crystal panel 100. As a result of the comparatively high energy applied using the laser beam LB, deterioration occurs in each of the members (the alignment layer, liquid crystal molecules, and so on, for example) in the test subject area AR of the liquid crystal panel 100. At this time, the degree of deterioration in the liquid crystal panel 100 differs according to the set variable parameter of the laser beam LB. In this embodiment, the main form of deterioration caused by irradiation of the laser beam LB that will be considered is alteration of the alignment layer in the test subject area AR, leading to localized deterioration in the alignment of the liquid crystal layer.

Figure 1B:
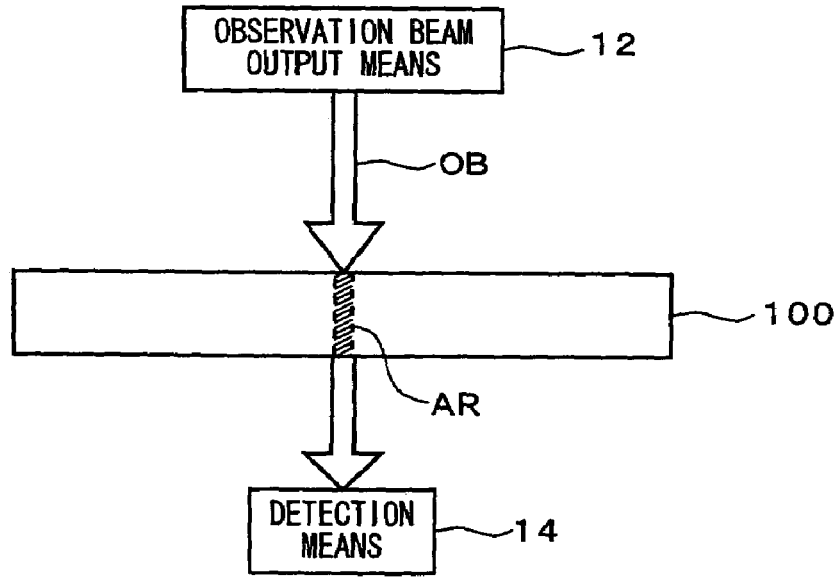

Next, as shown in FIG. 1B, the liquid crystal panel 100 is irradiated with an observation beam OB, and the condition of the observation beam OB after passing through the liquid crystal panel 100 is detected (second step). Here, the condition (optical characteristics) of the detection subject observation beam OB may be considered as the optical intensity, polarization state, spectral characteristic, and various other characteristics. Hence, observation beam output means 12 and detection means 14 are selected appropriately in accordance with the characteristics to be detected as the condition of the observation beam OB. At this time, if the test subject area AR of the liquid crystal panel 100 has deteriorated, in most cases different optical characteristics are detected in the test subject area AR to those detected in other areas.

The light fastness of the liquid crystal panel is then evaluated on the basis of differences in the condition of the observation beam OB corresponding to the set variable parameter of the laser beam LB (third step). For example, deterioration over time may be evaluated by comparing the difference in the condition of the observation beam OB corresponding to the irradiation duration of the laser beam LB. Further, the fastness of the liquid crystal panel 100 to optical intensity may be evaluated by comparing the difference in the condition of the observation beam OB corresponding to the irradiation energy of the laser beam LB.

Note that the laser beam LB may double as the observation beam OB such that the first and second steps described above are performed in parallel. Further, energy may be applied more efficiently by employing a continuous wave (CW) as the laser beam LB.

An outline of the liquid crystal panel testing method according to the present invention is as described above. Next, a more specific embodiment will be described. In the following detailed description of this embodiment, it is assumed that a liquid crystal panel with a TN (twisted nematic) alignment mode is used, and that the optical intensity of the observation beam OB is detected as the condition of the observation beam OB.

Figure 2A:
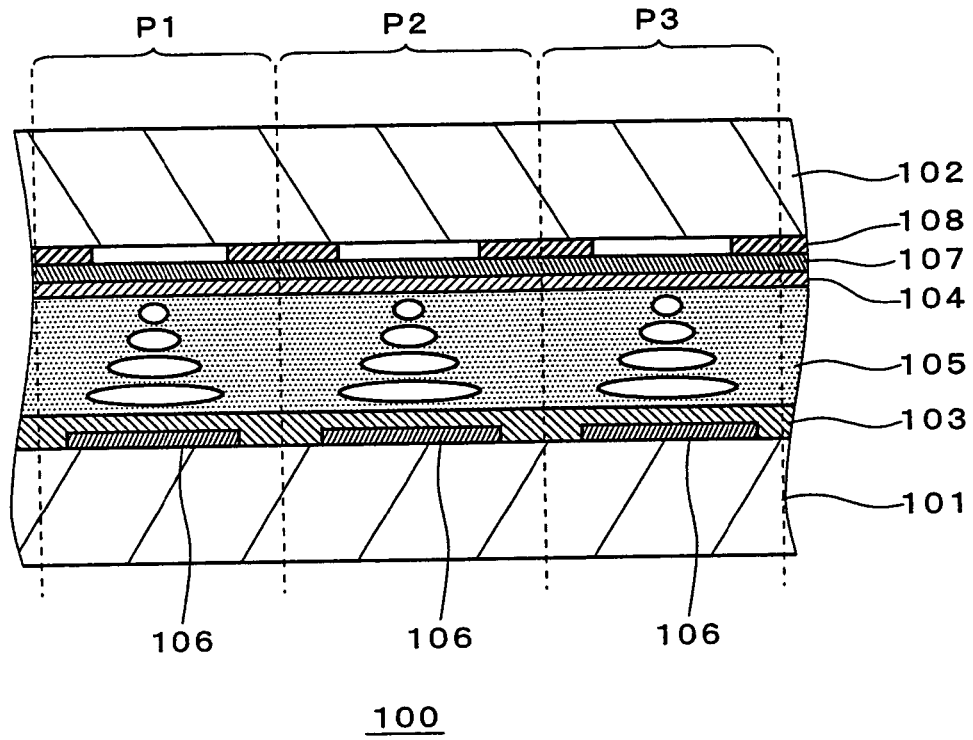
FIG. 2 is a sectional view illustrating a constitutional example of a liquid crystal panel serving as a test subject.
Figure 2B:
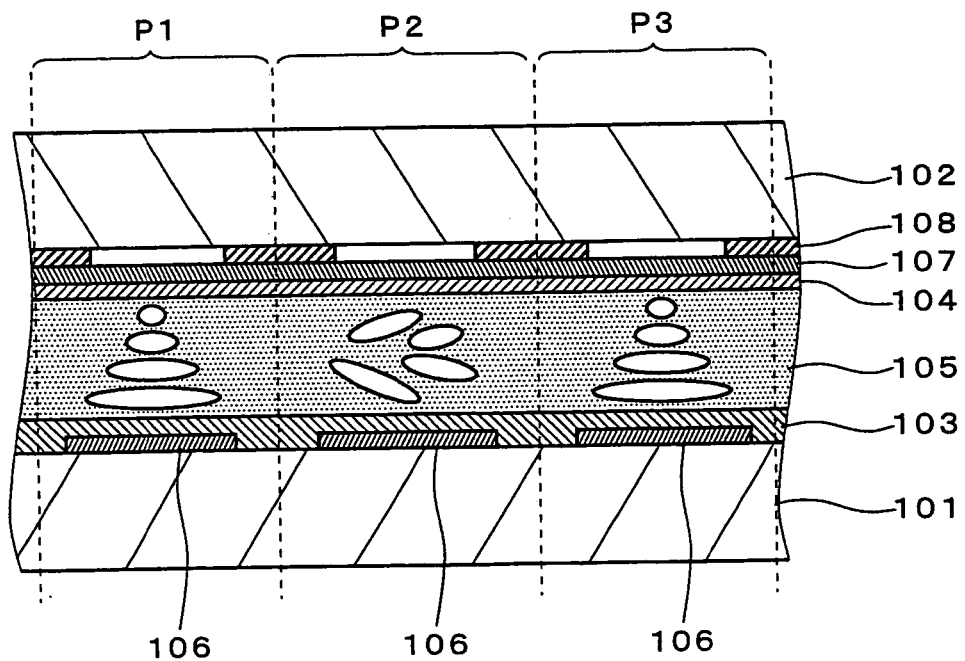

FIG. 2 is a sectional view illustrating a constitutional example of the liquid crystal panel 100 serving as the test subject. FIG. 2A is a schematic view showing the constitution of the liquid crystal panel 100 prior to deterioration, and FIG. 2B is a schematic view showing the constitution of the deteriorated liquid crystal panel 100.

The liquid crystal panel 100 shown in FIGS. 2A and 2B is constituted by substrates 101, 102, alignment layers 103, 104, a liquid crystal layer 105, pixel electrodes 106, a counter electrode 107, and a black mask 108. In FIG. 2, a part of the liquid crystal panel 100, specifically a region comprising three pixels P1, P2, P3, is illustrated, but the entire liquid crystal panel 100 is constituted by a large number of such pixels arranged in matrix form.

The substrates 101, 102 are constituted by a translucent material such as glass or plastic, and disposed opposite each other on either side of a spacer or the like, not shown in the drawing, with a predetermined gap (of approximately 3 μm, for example) therebetween.

The alignment layers 103, 104 serve to regulate the alignment of the liquid crystal molecules in the liquid crystal layer 105 interposed between the two substrates 101, 102. In this example, polyimide films subjected to a rubbing process are used as the alignment layers 103, 104. The alignment layers 103, 104 possess an alignment regulating force for aligning the liquid crystal molecules in the respective film surfaces thereof in parallel and in a single direction. By disposing the alignment layers 103, 104 such that the directions in which this alignment regulating force acts are substantially orthogonal, the liquid crystal molecules in the liquid crystal layer 105 are TN aligned.

The liquid crystal layer 105 is constituted by a nematic liquid crystal, and interposed between the substrates 101, 102. As shown in FIG. 2A, the liquid crystal molecules contained in the liquid crystal layer 105 are aligned so as to be twisted 90 degrees continuously from the substrate 101 side toward the substrate 102 side. When deterioration occurs in a part of the liquid crystal panel 100 (the part corresponding to the pixel P2, for example) due to a decrease in or disappearance of the alignment regulating force of the alignment layer 103 and/or 104 or the like, the alignment of the liquid crystal molecules in that part decreases as shown in FIG. 2B.

The pixel electrodes 106 serve to apply a voltage to each pixel of the liquid crystal layer 105, and are therefore formed in positions corresponding to each of the pixels P1 to P3 on the substrate 101. For example, the pixel electrodes 106 are formed by depositing a transparent conductive coating such as ITO (Indium-Tin-Oxide) on the substrate 101, and then patterning the coating. A switching element such as a thin film transistor (TFT), not shown in the drawing, is connected to each pixel electrode 106, and voltage application is controlled by this switching element. Each switching element is driven by an external circuit via a signal line.

The counter electrode 107 serves to apply a voltage to the liquid crystal layer 105 together with the pixel electrodes 106, and is formed over substantially the entire surface of the substrate 102. The counter electrode 107 is a common electrode shared by all of the pixels, and is connected to a predetermined potential such as a ground potential. A transparent conductive coating such as ITO may also be used for the counter electrode 107.

The black mask 108 covers the boundaries between the pixels to block light leaking out from these areas, and is formed on the substrate 102. The black mask 108 is formed using a material such as chromium, which has extremely poor light transmittivity, in lattice form such that the areas corresponding to each pixel are open.

Figure 3A:
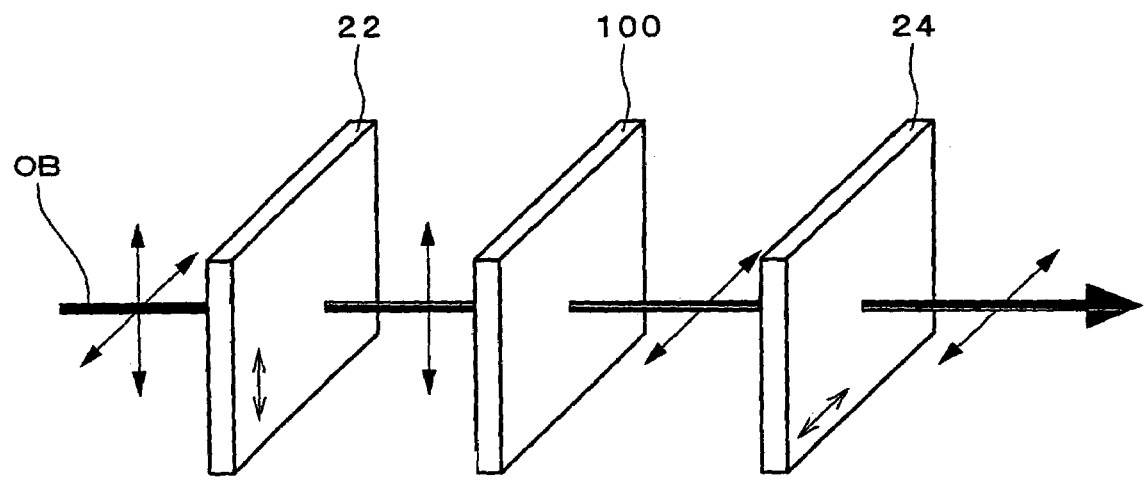
FIG. 3 is a view illustrating an example of a method for irradiating the liquid crystal panel with an observation beam, and detecting the optical intensity of the observation beam.
Figure 3B:
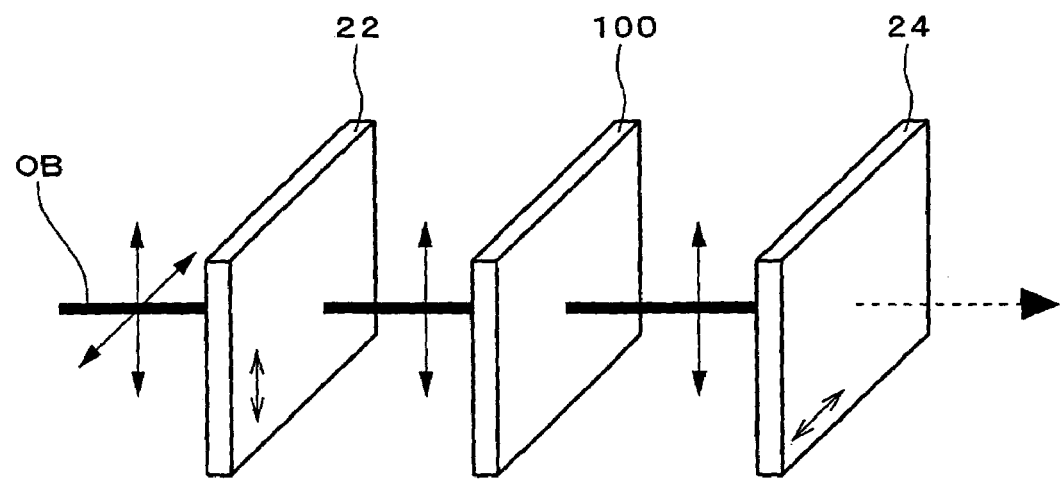

FIG. 3 is a view illustrating an example of a method for irradiating the liquid crystal panel 100 shown in FIG. 2 with an observation beam, and detecting the optical intensity of the observation beam. More specifically, FIG. 3A is a view illustrating this method in relation to the liquid crystal panel 100 prior to deterioration shown in FIG. 2A, and FIG. 3B is a view illustrating this method in relation to the deteriorated liquid crystal panel 100 shown in FIG. 2B.

As shown in FIG. 3A, polarization elements 22, 24 are disposed respectively on the light entrance side and light exit side of the liquid crystal panel 100. The polarization element 22 and the polarization element 24 are disposed such that the respective principal optical axes thereof are substantially orthogonal to each other. The polarization element 22 is disposed such that its principal optical axis (polarization axis) is substantially parallel to the average alignment direction (director) of the liquid crystal molecules on the substrate 101 side of the liquid crystal panel 100. The polarization element 24 is disposed such that its principal optical axis (polarization axis) is substantially parallel to the director on the substrate 102 side of the liquid crystal panel 100. Of the observation beam OB that enters the polarization element 22, only the oscillation component along the principal optical axis of the polarization element 22 passes through the polarization element 22 to become linearly polarized light. When the observation beam OB enters one surface (on the substrate 101 side) of the liquid crystal panel 101 as linearly polarized light, the polarization direction thereof is rotated 90 degrees along the twist of the liquid crystal molecules, whereupon the observation beam OB emerges from the other surface (the substrate 102 side) of the liquid crystal panel 100. After the observation beam OB emerges from the liquid crystal panel 100, the polarization direction thereof is substantially parallel to the principal optical axis of the polarization element 24, and hence the observation beam OB passes through the polarization element 24.

In the example shown in FIG. 3B, the relative positions of the liquid crystal panel 100 and the polarization elements 22, 24 are similar to those shown in FIG. 3A. However, as shown in FIG. 2B, the alignment of the liquid crystal molecules in the liquid crystal layer 105 of the pixel P2 has decreased, and hence the ability to rotate the polarization direction of the incident light (the optical rotating power) decreases correspondingly. When the alignment of the liquid crystal molecules has decreased to a certain extent, the observation beam OB emerges from the other surface of the liquid crystal panel 100 with almost no rotation of its polarization direction, as shown in FIG. 3B. As a result, after the observation beam OB emerges from the liquid crystal panel 100, its polarization direction is substantially orthogonal to the principal optical axis of the polarization element 24, and hence the observation beam OB cannot pass through the polarization element 24.

By employing the polarization elements 22, 24 in this manner, the optical intensity of the observation beam OB that passes through the liquid crystal panel 100 can be detected. Note that in cases such as when the laser beam LB doubles as the observation beam OB such that the polarization state of the observation beam OB itself corresponds to linearly polarized light, the polarization element 22 disposed on the light entrance side of the liquid crystal panel 100 becomes unnecessary.

Next, a preferred constitutional example of a testing apparatus used to implement the liquid crystal panel testing method according to the above embodiment will be described.

Figure 4:
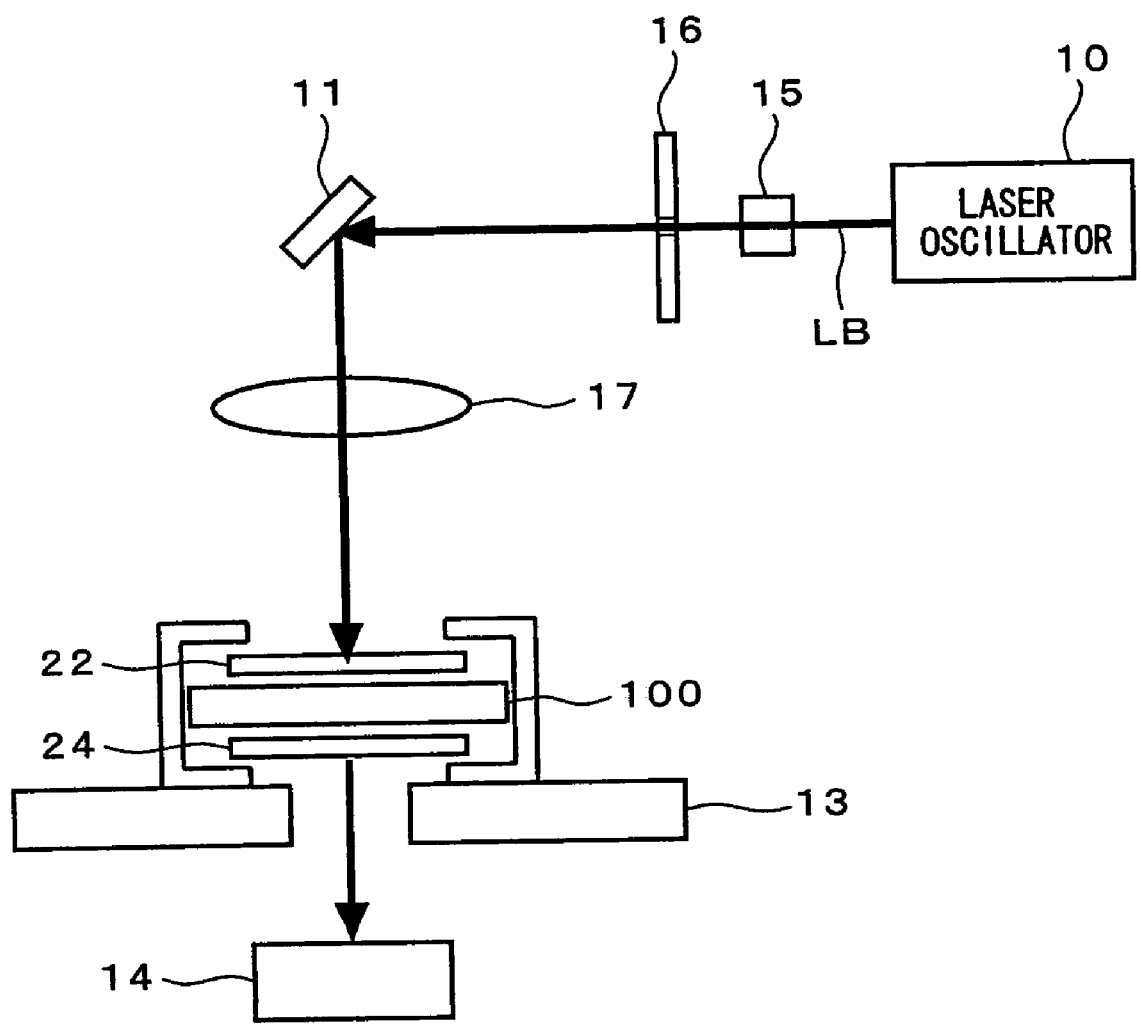
FIG. 4 is a view illustrating a constitutional example of a liquid crystal panel testing apparatus.

FIG. 4 is a view illustrating a constitutional example of a liquid crystal panel testing apparatus. A liquid crystal panel testing apparatus 1 shown in FIG. 4 is used to test the light fastness of a liquid crystal panel in accordance with the testing method described above, and comprises the laser oscillator 10, a mirror 11, a table 13, a power meter (detection means) 14, a homogenizer 15, a mask 16, an image-forming lens 17, and the polarization elements 22, 24.

The laser oscillator 10 is a light source capable of outputting the laser beam LB with at least one of the wavelength, irradiation energy, and irradiation duration of the laser beam LB set as a variable parameter. Any device which is capable of producing the desired amount of deterioration in the liquid crystal panel 100 over a short time period may be used as the laser oscillator 10. In this embodiment, for example, a semiconductor laser which outputs a continuous wave laser beam with a wavelength of 405 nm is used. The laser oscillator 10 of this embodiment also functions as observation beam output means for irradiating the liquid crystal panel 100 with an observation beam for measuring the light transmitting condition of the liquid crystal panel 100.

The mirror 11 reflects the laser beam LB output from the laser oscillator 10, thereby altering the course of the laser beam LB to the direction of the table 13 on which the liquid crystal panel 100 is placed.

The table 13 carries the liquid crystal panel 100 serving as the test subject, and sets the relative positions of the laser beam LB and liquid crystal panel 100 so that the test subject area of the liquid crystal panel 100 is irradiated with the laser beam LB. The table 13 supports the liquid crystal panel 100 and the polarization elements 22, 24 by means of a folder, and is thus capable of moving the liquid crystal panel 100 and polarization elements 22, 24 freely in a three-dimensional direction. Hence, the table 13 functions as position setting means for setting the relative positions of the liquid crystal panel 100 and laser beam LB.

The power meter 14 detects the optical intensity, i.e. the condition, of the observation beam (in this embodiment, the laser beam LB doubles as the observation beam) after passing through the liquid crystal panel 100. In this embodiment, deterioration in the liquid crystal panel 100 can be observed as variation in the intensity of the transmitted light using the polarization elements 22, 24.

The homogenizer 15 converts the laser beam LB that is output from the laser oscillator 10 such that the intensity distribution thereof is substantially uniform.

The mask 16 converts the beam shape of the laser beam LB after passing through the homogenizer 15 into a substantially rectangular shape.

Figures 5A, 5B:
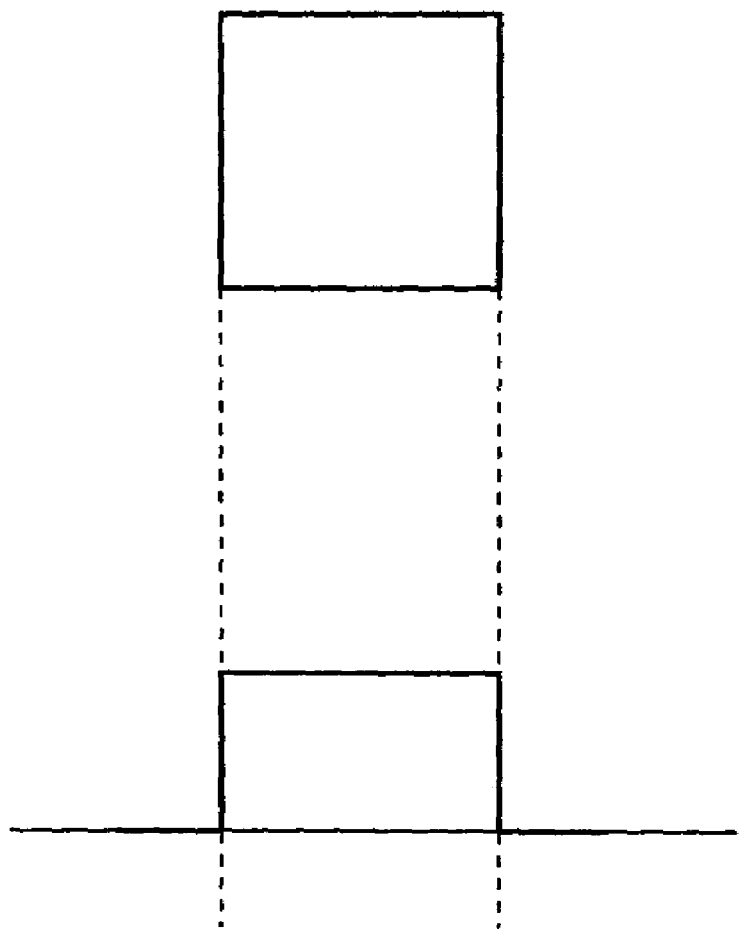
FIG. 5 is a view illustrating the condition of a laser beam after passing through an image-forming optical system.

The image-forming lens 17 forms an image of the laser light LB, the intensity distribution and beam shape of which are reshaped after passing through the homogenizer 15 and mask 16, on the test subject area of the liquid crystal panel 100. FIG. 5 is a view illustrating the condition of the laser beam LB after passing through this image-forming optical system. The beam shape of the laser beam LB is substantially rectangular, as shown in FIG. 5A, and the intensity distribution thereof is substantially uniform from the beam center to the beam ends, as shown in FIG. 5B.

The polarization element 22 is disposed on the light entrance side of the liquid crystal panel 100, and transmits only the oscillation component of the incident light which is co-directional with the polarization axis. Similarly, the polarization element 24 is disposed on the light exit side of the liquid crystal panel 100, and transmits only the oscillation component of the light that emerges from the liquid crystal panel 100 which is co-directional with the polarization axis. The gap between the polarization elements 22, 24 and the relative positions of the polarization elements 22, 24 and the liquid crystal panel 100 may be set as desired. In this embodiment, the polarization elements 22, 24 and liquid crystal panel 100 are disposed as shown in FIG. 3. Using the polarization elements 22, 24, the optical intensity of the observation beam after passing through the liquid crystal panel 100 can be detected as the condition of the observation beam.

Note that in cases such as when the laser beam LB that enters the liquid crystal panel 100 is originally linearly polarized light, the light entrance side polarization element 22 is unnecessary. Moreover, when a liquid crystal panel 100 attached with polarization elements (in its final manufactured state or the like) is used as the test subject, both of the polarization elements are unnecessary.

Using this liquid crystal panel testing apparatus 1, the liquid crystal panel 100 is caused to deteriorate by being irradiated with a laser beam having conditions such as the wavelength and irradiation duration set variously, and by monitoring the transmitted light using the laser beam in parallel as an observation beam, the light fastness of the liquid crystal panel 100 can be evaluated. By plotting a graph on which the abscissa shows the laser beam irradiation duration and the ordinate shows the intensity (transmittivity) of the light that passes through the liquid crystal panel 100, for example, the light fastness of the liquid crystal panel can be evaluated. By calculating an acceleration factor from the evaluation result, the useful life of the liquid crystal panel 100 can be estimated.

Figure 6:
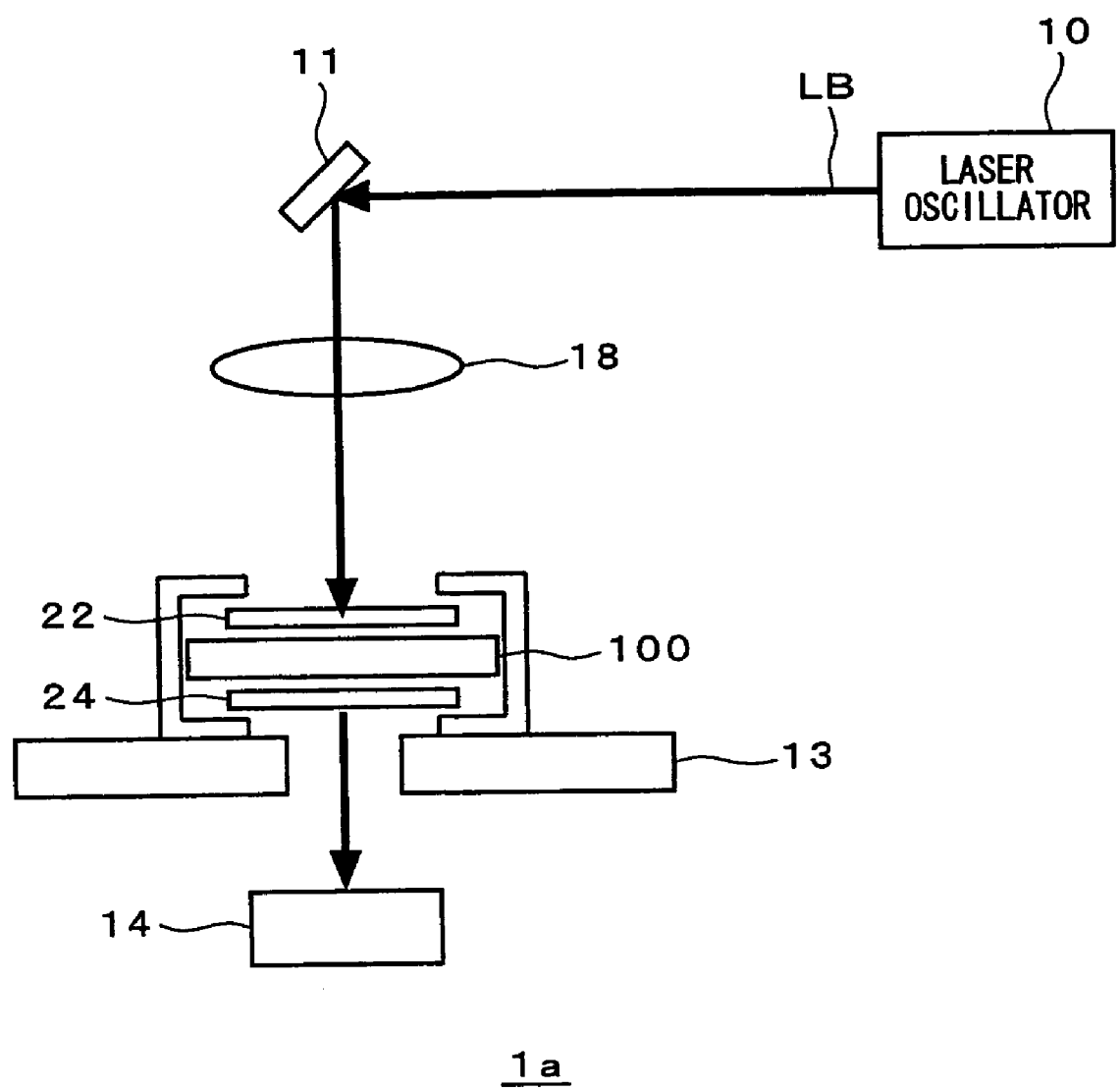
FIG. 6 is a view illustrating another constitutional example of a liquid crystal panel testing apparatus.

FIG. 6 is a view illustrating another constitutional example of a liquid crystal panel testing apparatus. The basic constitution of a liquid crystal panel testing apparatus 1a shown in FIG. 6 is similar to that of the testing apparatus 1 (see FIG. 4) described above. Accordingly, common constitutional elements have been allocated identical reference numerals, and description thereof has been omitted.

The testing apparatus 1a of this example, shown in FIG. 6, differs from the testing apparatus 1 described above in that the image-forming optical system of the testing apparatus 1 is replaced with a condensing optical system. More specifically, the homogenizer 15 and mask 16 are omitted, and the image-forming lens 17 is replaced with a condensing lens 18.

Figures 7A, 7B:
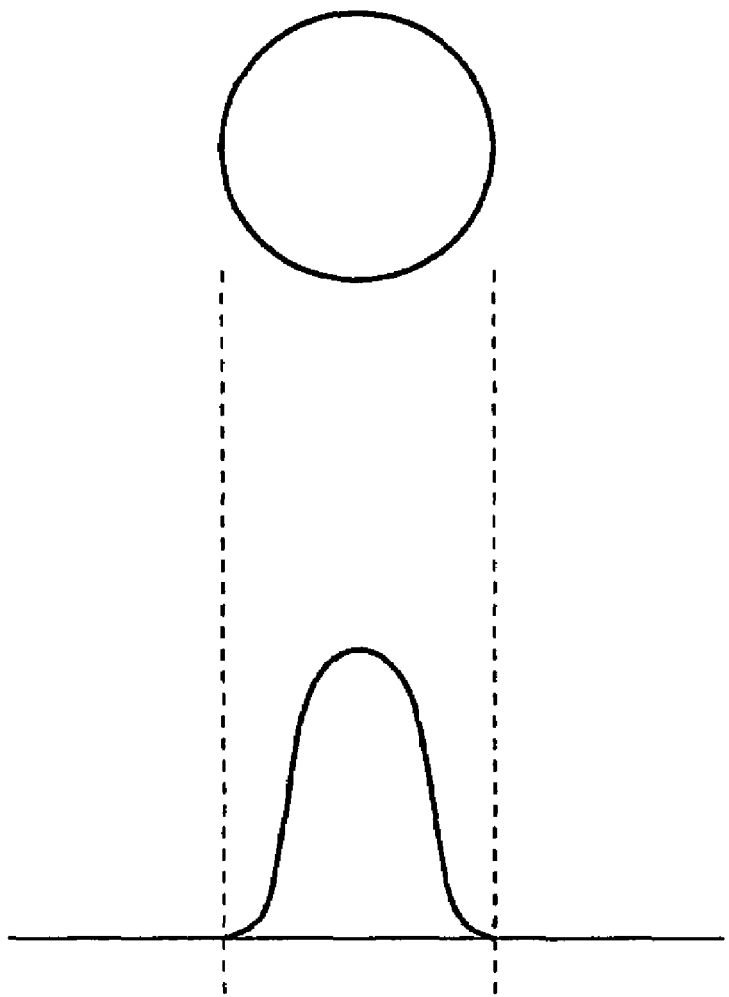
FIG. 7 is a view illustrating the condition of the laser beam after passing through a condensing optical system.

The mirror 11 alters the course of the laser beam LB, after which the laser beam LB enters the condensing lens 18 to be condensed. Thus, in the testing apparatus 1a of this embodiment, shown in FIG. 6, a constitution in which the test subject area of the liquid crystal panel 100 is irradiated with the laser beam LB via the condensing optical system using the condensing lens 18 is employed. FIG. 7 is a view illustrating the condition of the laser beam LB after passing through the condensing optical system. The beam shape of the laser beam LB is substantially circular, as shown in FIG. 7A, and the intensity distribution thereof is such that the energy near the center of the beam is high, as shown in FIG. 7B.

According to this embodiment, a laser beam is used as the light for checking the light fastness of the liquid crystal panel, and therefore light irradiation can be performed with a higher localized energy density than a case where a halogen lamp or the like is used as a light source. As a result, a deterioration phenomenon can be elicited in an extremely short time (between several minutes and several tens of minutes, for example), and the light fastness of the liquid crystal panel can be evaluated by investigating the correlation between the irradiation conditions of the laser light during the irradiation and the degree of deterioration produced by the irradiation. Hence, the amount of time required to evaluate the light fastness of the liquid crystal panel can be reduced greatly.

Furthermore, by using a laser beam, a constitutional element serving as the evaluation subject of the liquid crystal panel can be irradiated locally with light and thus caused to deteriorate. In so doing, elements other than the evaluation subject element are almost entirely unaffected, and hence a highly precise evaluation result can be obtained. Moreover, tests can be performed easily on a plurality of locations within a single liquid crystal panel.

Moreover, by using a laser beam, the energy density of the light that is emitted onto the test subject area can easily be made uniform, and hence an accurate evaluation can be obtained easily in an acceleration test.

Note that the present invention is not limited to the content of the embodiments described above, and various modifications may be made within the scope of the present invention.

For example, in the embodiments described above, the optical intensity is used as the condition of the observation beam, but the polarization state, spectral characteristic, retardation, and various other characteristics may be used instead. In such cases, detection means which correspond to the condition to be detected should be used. For example, if variation in the polarization state is to be detected, an ellipsometer is used as the detection means, and if the spectral characteristic is to be detected, a spectrometer is used as the detection means.

Further, in the embodiments described above, the laser beam LB doubles as an observation beam, but the laser beam and observation beam may be provided separately. In this case, first the liquid crystal panel is caused to deteriorate using the laser beam, and then the optical characteristics of the test subject area are detected using the separate observation beam.

Further, in the embodiments described above, a TN alignment mode liquid crystal panel is cited as an example, but the scope of application of the present invention is not limited thereto, and the present invention may also be applied in a light fastness test for other types of liquid crystal panel (an STN type or the like, for example).

We claim:

1. A liquid crystal panel testing method for testing a light fastness of a liquid crystal panel comprising a pair of substrates and a liquid crystal layer interposed between said substrates, the method comprising:
   (a) irradiating a test subject area of said liquid crystal panel with a laser beam, with at least one of a wavelength, an irradiation energy, and an irradiation duration of said laser beam set as a variable parameter;
   (b) irradiating said liquid crystal panel with an observation beam and detecting an intensity of said observation beam after passing through said liquid crystal panel; and
   (c) determining the light fastness of said liquid crystal panel based on a difference in the intensity of said observation beam and an intensity of the laser beam corresponding to the setting of said variable parameter of said laser beam;
   wherein, in said (a), an alignment of said liquid crystal layer in said test subject area decreases locally upon irradiation with said laser beam.

2. The liquid crystal panel testing method according to claim 1, wherein, in said (b), a polarization element is disposed on at least a light exit side of said liquid crystal panel, and an optical intensity of said observation beam after passing through said polarization element is detected as the intensity of said observation beam.

3. The liquid crystal panel testing method according to claim 1, wherein said laser beam doubles as said observation beam, and said (a) and said (b) are performed in parallel.

4. The liquid crystal panel testing method according to claim 1, wherein said laser beam is set as a continuous wave.

5. The liquid crystal panel testing method according to claim 1, wherein, in said (a), said test subject area is irradiated with said laser beam via a image-forming optical system.

6. The liquid crystal panel testing method according to claim 1, wherein, in said (a), said test subject area is irradiated with said laser beam via a condensing optical system.

* * * * *